(12) United States Patent
Horton et al.

(10) Patent No.: US 11,666,357 B2
(45) Date of Patent: Jun. 6, 2023

(54) ENCLOSURE FOR ELECTRONICS OF A SURGICAL INSTRUMENT

(71) Applicant: COVIDIEN LP, Mansfield, MA (US)

(72) Inventors: Titus Horton, Lyons, CO (US); Jeremy P. Green, Westminster, CO (US); Weng-Kai K. Lee, Niwot, CO (US); Daniel Simmons, Broomfield, CO (US); Terry M. Duffin, Westminster, CO (US)

(73) Assignee: Covidien LP, Mansfield, MA (US)

( * ) Notice: Subject to any disclaimer, the term of this patent is extended or adjusted under 35 U.S.C. 154(b) by 777 days.

(21) Appl. No.: 16/572,157

(22) Filed: Sep. 16, 2019

(65) Prior Publication Data

US 2021/0077141 A1 Mar. 18, 2021

(51) Int. Cl.
*A61B 17/32* (2006.01)
*H05K 5/06* (2006.01)
*A61B 17/00* (2006.01)

(52) U.S. Cl.
CPC ..... *A61B 17/320068* (2013.01); *H05K 5/066* (2013.01); *A61B 2017/00477* (2013.01); *A61B 2017/00526* (2013.01); *A61B 2017/00734* (2013.01)

(58) Field of Classification Search
CPC .. A61B 17/320068; A61B 2017/00477; A61B 2017/00526; A61B 2017/00734; H05K 5/068
See application file for complete search history.

(56) References Cited

U.S. PATENT DOCUMENTS

| 1,813,902 A | 7/1931 | Bovie |
| 2,874,470 A | 2/1959 | Richards |
| 2,990,616 A | 7/1961 | Balamuth |
| 3,432,691 A | 3/1969 | Shoh |
| 3,489,930 A | 1/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,193,818 A | 3/1980 | Young et al. |
| 4,227,110 A | 10/1980 | Douglas et al. |
| 4,300,083 A | 11/1981 | Heiges |
| 4,302,728 A | 11/1981 | Nakamura |
| 4,370,302 A | 1/1983 | Suzuoka et al. |
| 4,641,053 A | 2/1987 | Takeda |
| 5,113,116 A | 5/1992 | Wilson |
| 5,224,680 A | 7/1993 | Greenstein et al. |

(Continued)

*Primary Examiner* — Carl J Arbes
(74) *Attorney, Agent, or Firm* — Carter, DeLuca & Farrell LLP

(57) ABSTRACT

An enclosure configured to hermetically seal electronics of a surgical instrument therein includes a first casing component defining a first weld deck about a perimeter thereof, a second casing component defining a second weld deck about a perimeter thereof, and an energy director extending from the first weld deck and configured to facilitate ultrasonic welding of the first and second weld decks of the first and second casing components, respectively, with one another to establish a weld seam hermetically sealing the first and second casing components. The first weld deck lies in multiple planes.

20 Claims, 5 Drawing Sheets

(56) References Cited

U.S. PATENT DOCUMENTS

| | | |
|---|---|---|
| 5,264,925 A | 11/1993 | Shipp et al. |
| 5,275,166 A | 1/1994 | Vaitekunas et al. |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,565,520 A | 10/1996 | Fock et al. |
| 5,582,617 A | 12/1996 | Klieman et al. |
| 5,593,414 A | 1/1997 | Shipp et al. |
| 5,685,311 A | 11/1997 | Hara |
| 5,717,306 A | 2/1998 | Shipp |
| 5,728,130 A | 3/1998 | Ishikawa et al. |
| 5,792,138 A | 8/1998 | Shipp |
| 5,796,056 A | 8/1998 | Bredow et al. |
| 5,810,859 A | 9/1998 | DiMatteo et al. |
| 5,858,018 A | 1/1999 | Shipp et al. |
| 5,873,873 A | 2/1999 | Smith et al. |
| 5,897,569 A | 4/1999 | Kellogg et al. |
| 5,910,152 A | 6/1999 | Bays |
| 5,938,633 A | 8/1999 | Beaupre |
| 5,944,737 A | 8/1999 | Tsonton et al. |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt et al. |
| 6,095,981 A | 8/2000 | McGahan |
| 6,141,205 A * | 10/2000 | Nutzman ............ A61N 1/3956 361/528 |
| 6,162,194 A | 12/2000 | Shipp |
| 6,183,426 B1 | 2/2001 | Akisada et al. |
| 6,220,098 B1 | 4/2001 | Johnson et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,284,185 B1 | 9/2001 | Tokuda et al. |
| 6,287,344 B1 | 9/2001 | Wampler et al. |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer et al. |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,482,220 B1 | 11/2002 | Mueller |
| 6,491,708 B2 | 12/2002 | Madan et al. |
| 6,500,188 B2 | 12/2002 | Harper et al. |
| 6,514,267 B2 | 2/2003 | Jewett |
| 6,537,291 B2 | 3/2003 | Friedman et al. |
| 6,561,983 B2 | 5/2003 | Cronin et al. |
| 6,565,520 B1 | 5/2003 | Young |
| 6,588,277 B2 | 7/2003 | Giordano et al. |
| 6,589,200 B1 | 7/2003 | Schwemberger et al. |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener et al. |
| 6,719,776 B2 | 4/2004 | Baxter et al. |
| 6,752,815 B2 | 6/2004 | Beaupre |
| 6,773,444 B2 | 8/2004 | Messerly |
| 6,776,499 B2 | 8/2004 | Chang |
| 6,819,506 B1 | 11/2004 | Taylor et al. |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany et al. |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger et al. |
| 7,163,548 B2 | 1/2007 | Stulen et al. |
| 7,179,254 B2 | 2/2007 | Pendekanti et al. |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,217,893 B1 | 5/2007 | Huang et al. |
| 7,230,199 B2 | 6/2007 | Chou et al. |
| 7,244,262 B2 | 7/2007 | Wiener et al. |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 7,534,002 B2 | 5/2009 | Yamaguchi et al. |
| 7,670,030 B2 | 3/2010 | Klipstein |
| 7,977,587 B2 | 7/2011 | Rajagopal et al. |
| 9,017,355 B2 | 4/2015 | Smith et al. |
| 9,271,633 B2 | 3/2016 | Scott et al. |
| 9,368,004 B2 | 6/2016 | Plaven |
| 10,588,231 B2 * | 3/2020 | Sgroi, Jr. ............ A61B 17/1155 |
| 2002/0002379 A1 | 1/2002 | Bishop |
| 2002/0077645 A1 | 6/2002 | Wiener et al. |
| 2002/0091339 A1 | 7/2002 | Horzewski et al. |
| 2002/0138090 A1 | 9/2002 | Jewett |
| 2003/0144680 A1 | 7/2003 | Kellogg et al. |
| 2003/0149424 A1 | 8/2003 | Barlev et al. |
| 2003/0199794 A1 | 10/2003 | Sakurai et al. |
| 2003/0212363 A1 | 11/2003 | Shipp |
| 2004/0062047 A1 | 4/2004 | Camarota et al. |
| 2004/0067038 A1 | 4/2004 | Popovic |
| 2004/0097972 A1 | 5/2004 | Shipp et al. |
| 2004/0116952 A1 | 6/2004 | Sakurai et al. |
| 2004/0256487 A1 | 12/2004 | Collins et al. |
| 2005/0047114 A1 | 3/2005 | Harrell et al. |
| 2005/0091770 A1 | 5/2005 | Mourad et al. |
| 2005/0107658 A1 | 5/2005 | Brockway |
| 2005/0113815 A1 | 5/2005 | Ritchie et al. |
| 2005/0119677 A1 | 6/2005 | Shipp |
| 2005/0149063 A1 | 7/2005 | Young et al. |
| 2005/0203329 A1 | 9/2005 | Muto et al. |
| 2005/0234338 A1 | 10/2005 | Masuda |
| 2005/0234484 A1 | 10/2005 | Houser et al. |
| 2006/0012299 A1 | 1/2006 | Suehiro et al. |
| 2006/0058825 A1 | 3/2006 | Ogura et al. |
| 2006/0079878 A1 | 4/2006 | Houser |
| 2006/0079879 A1 | 4/2006 | Faller et al. |
| 2006/0087286 A1 | 4/2006 | Phillips et al. |
| 2006/0129168 A1 | 6/2006 | Shipp |
| 2006/0178579 A1 | 8/2006 | Haynes |
| 2006/0178667 A1 | 8/2006 | Sartor et al. |
| 2006/0194567 A1 | 8/2006 | Kelly et al. |
| 2006/0206100 A1 | 9/2006 | Eskridge et al. |
| 2006/0217729 A1 | 9/2006 | Eskridge et al. |
| 2007/0011836 A1 | 1/2007 | Brewer et al. |
| 2007/0126994 A1 | 6/2007 | Hwang |
| 2007/0149881 A1 | 6/2007 | Rabin |
| 2007/0166663 A1 | 7/2007 | Telles et al. |
| 2007/0175960 A1 | 8/2007 | Shelton et al. |
| 2007/0224571 A1 | 9/2007 | Watson |
| 2007/0227866 A1 | 10/2007 | Dimig |

(56) References Cited

U.S. PATENT DOCUMENTS

| | | |
|---|---|---|
| 2007/0239028 A1 | 10/2007 | Houser et al. |
| 2007/0239101 A1 | 10/2007 | Kellogg |
| 2008/0033248 A1 | 2/2008 | Akagi |
| 2008/0049445 A1 | 2/2008 | Harbers |
| 2008/0051693 A1 | 2/2008 | Babaev |
| 2008/0245841 A1 | 10/2008 | Smith et al. |
| 2009/0116243 A1 | 5/2009 | Condon et al. |
| 2009/0138006 A1 | 5/2009 | Bales et al. |
| 2009/0143797 A1 | 6/2009 | Smith et al. |
| 2009/0143805 A1 | 6/2009 | Palmer et al. |
| 2009/0223033 A1 | 9/2009 | Houser |
| 2010/0004669 A1 | 1/2010 | Smith et al. |
| 2010/0008082 A1 | 1/2010 | Brass et al. |
| 2011/0141731 A1 | 6/2011 | Chang |
| 2011/0235313 A1 | 9/2011 | Canella |
| 2012/0010709 A1 | 1/2012 | Wilson et al. |
| 2012/0033411 A1 | 2/2012 | Heo |
| 2012/0179159 A1 | 7/2012 | Krapohl |
| 2013/0049041 A1 | 2/2013 | Ramer et al. |
| 2013/0128496 A1 | 5/2013 | Chien et al. |
| 2013/0170216 A1 | 7/2013 | Li |
| 2014/0309499 A1 | 10/2014 | Swift |
| 2014/0338504 A1 | 11/2014 | Beer et al. |

\* cited by examiner

ENCLOSURE FOR ELECTRONICS OF A SURGICAL INSTRUMENT

BACKGROUND

Technical Field

The present disclosure relates to surgical instruments and, more particularly, to enclosures for electronics of surgical instruments, e.g., ultrasonic surgical generators of ultrasonic surgical instruments, and methods of manufacturing the same.

Background of Related Art

Ultrasonic surgical instruments utilize ultrasonic energy, e.g., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer along a waveguide to an end effector that is spaced-apart from the generator and transducer. Cordless ultrasonic surgical instruments employ a portable power source, e.g., a battery pack, and a generator and transducer assembly that are mounted on or within a handle of the instrument itself, while the waveguide interconnects the generator and transducer assembly with the end effector.

After use of an ultrasonic surgical instrument such as, for example, a cordless ultrasonic surgical instrument, the battery and/or the generator and transducer assembly may be sterilized and reused. Sterilization processes may involve high pressure, extreme heat, and/or moisture that could damage internal electronics of these components.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, an enclosure configured to hermetically seal electronics of a surgical instrument therein is provided. The enclosure includes a first casing component defining a first weld deck about a perimeter thereof, a second casing component defining a second weld deck about a perimeter thereof, and an energy director. The energy director extends from the first weld deck and is configured to facilitate ultrasonic welding of the first and second weld decks of the first and second casing components, respectively, with one another to establish a weld seam hermetically sealing the first and second casing components. The first weld deck lies in multiple planes.

In an aspect of the present disclosure, the energy director defines a maximum width less than a width of the first weld deck.

In another aspect of the present disclosure, the first weld deck includes first and second planar portions disposed on first and second sides of the energy director.

In still another aspect of the present disclosure, the energy director defines a maximum width to height ratio of about 0.75:1.0 to about 1.0:0.75.

In yet another aspect of the present disclosure, the energy director defines an apex angle of from about 45 to about 75 degrees.

In another aspect of the present disclosure, the first and second casing components are formed from PPSU.

A surgical enclosure provided in accordance with aspects of the present disclosure includes electronics including at least one visual indicator and at least a first casing component enclosing the electronics therein. The first casing component is formed from a substantially transparent material and includes a first portion and a second portion. The first portion is treated to define a first finish that reduces transparency of the first portion. The second portion defines a greater transparency relative to the first portion to enable visualization of the at least one visual indicator therethrough.

In an aspect of the present disclosure, the first portion is treated to define the first finish via laser etching.

In another aspect of the present disclosure, the second portion is treated to define a second finish different from the first finish.

In yet another aspect of the present disclosure, the first and second portions are treated via laser etching at different powers to achieve the first and second finishes, respectively. In such aspects, the first power may be at least 10 Watts and the second power may be at most 6 Watts.

In still another aspect of the present disclosure, the substantially transparent material is transparent PPSU.

In still yet another aspect of the present disclosure, the at least one visual indicator includes at least one LED, OLED, or incandescent light source.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
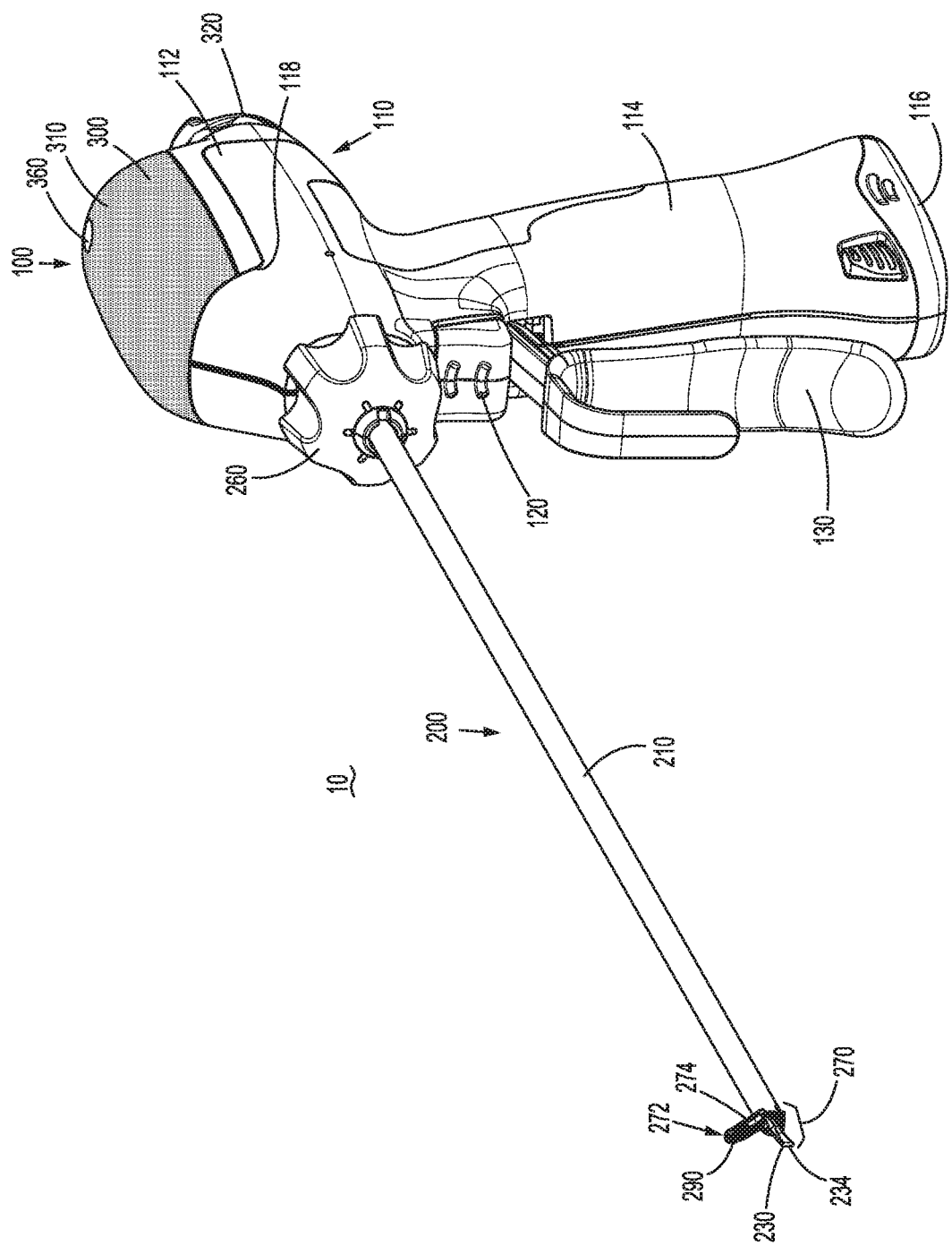
FIG. 1 is a front, perspective view of an ultrasonic surgical instrument provided in accordance with the present disclosure.

Referring generally to FIG. 1, an ultrasonic surgical instrument provided in accordance with the aspects and features of the present disclosure is shown generally identified by reference numeral 10. Although detailed hereinbelow with respect to ultrasonic surgical instrument 10, the aspects and features of the present disclosure are equally applicable for use with any suitable surgical instrument. For the purposes herein, ultrasonic surgical instrument 10 is generally described.

Ultrasonic surgical instrument 10 includes a handle assembly 100 and an elongated assembly 200 extending distally from handle assembly 100. Handle assembly 100 includes a housing 110 defining a body portion 112 configured to support an ultrasonic transducer and generator assembly ("TAG") 300, and a fixed handle portion 114 defining an internal compartment configured to receive a battery assembly (not shown). Handle assembly 100 further includes an activation button 120 operably positioned to electrically couple between TAG 300 and the battery assembly when TAG 300 is mounted on body portion 112 of housing 110 and the battery assembly is engaged within the internal compartment of fixed handle portion 114 of housing 110. A clamp trigger 130 extends from housing 110 of handle assembly 100 adjacent fixed handle portion 114 of housing 110. Clamp trigger 130 extends into body portion 112 of housing 110 and is selectively movable relative to housing 110 to actuate ultrasonic surgical instrument 10.

TAG 300 and the battery assembly, as noted above, are each removable from handle assembly 100 to facilitate disposal of handle assembly 100 after a single use or to enable sterilization of handle assembly 100 for subsequent use. TAG 300 may be configured to withstand sterilization such that TAG 300 may be sterilized for repeated use. The battery assembly may likewise be configured to withstand sterilization such that the battery assembly may be sterilized for repeated use. Alternatively, the battery assembly may be configured to be aseptically transferred and retained within the internal compartment of fixed handle portion 114 of housing 110 of handle assembly 100 such that the battery assembly may be repeatedly used without requiring sterilization thereof. A locking door 116 provides selective access to the internal compartment of fixed handle portion 114 to enable the insertion and removal of the battery assembly from fixed handle portion 114 of housing 110 and retains the battery assembly within the internal compartment when disposed in the locked condition.

Activation button 120, TAG 300, and the battery assembly are electrical coupled to one another upon engagement of TAG 300 with body portion 112 of housing 110 of handle assembly 100 and engagement of the battery assembly within the internal compartment of fixed handle portion 114 of housing 110. As such, in use, when activation button 120 is activated in an appropriate manner, an underlying two-mode switch assembly (not shown) is activated to supply power from the battery assembly to TAG 300 in either a "LOW" power mode or a "HIGH" power mode, depending upon the manner of activation of activation button 120.

TAG 300, described in greater detail below, includes a generator assembly 310 and an ultrasonic transducer assembly 320 (see FIG. 2). The ultrasonic transducer assembly 320 (FIG. 2) converts a high voltage AC signal received from the generator assembly 310 into mechanical motion that is output to elongated assembly 200, as detailed below.

Continuing with reference to FIG. 1, elongated assembly 200 includes an outer drive sleeve 210, an inner support sleeve (not shown) disposed within outer drive sleeve 210 and about which outer drive sleeve 210 is configured to slide, a waveguide 230 extending through the inner support sleeve, a rotation knob 260, and an end effector 270 disposed at the distal end of the inner support sleeve. Elongated assembly 200 is configured such that mechanical motion output from the ultrasonic transducer of TAG 300 is transmitted along waveguide 230 to end effector 270 for treating tissue therewith, such that clamp trigger 130 is selectively actuatable to manipulate end effector 270, and such that rotation knob 260 is selectively rotatable to rotate elongated assembly 200 relative to handle assembly 100. Elongated assembly 200 may be configured as a disposable, single-use component or a reusable component that is sterilizable for subsequent use and may be releasably engagable with handle assembly 100 or permanently affixed thereto.

Outer drive sleeve 210 is operably coupled to clamp trigger 130 within handle assembly 100 at a proximal end portion of outer drive sleeve 210 and is operably coupled with jaw member 272 of end effector 270 at a distal end portion of outer drive sleeve 210. The inner support sleeve 220 supports jaw member 272 at a distal end thereof. As a result of this configuration, actuation of clamp trigger 130 translates outer drive sleeve 210 about the inner support sleeve and urges jaw member 272 to pivot relative to inner support sleeve 220 and blade 234 of waveguide 230 between an open position and a clamping position for clamping tissue between jaw member 272 and blade 234 of waveguide 230. Alternatively, the configuration of outer drive sleeve 210 and the inner support sleeve may be reversed.

Waveguide 230 defines a body (not shown) and a blade 234 extending from the distal end of the body. The body of waveguide 230 is operably coupled to ultrasonic transducer assembly 320 (FIG. 2) of TAG 300 within handle assembly 100 and extends distally from handle assembly 100 through the inner support sleeve. Blade 234 extends from the body of waveguide 230 and distally from the inner support sleeve and forms part of end effector 270 in that blade 234 is positioned to oppose jaw member 272 such that pivoting of jaw member 272 from the open position to the clamping position enables clamping of tissue between jaw member 272 and blade 234. Blade 234 defines a curved configuration wherein the directions of movement of jaw member 272 between the open and clamping positions are perpendicular to the direction of curvature of blade 234. However, it is also contemplated that blade 234 define a straight configuration or that blade 234 curve towards or away from jaw member 272, that is, where the directions of movement of jaw member 272 between the open and clamping positions are coaxial or parallel to the direction of curvature of blade 234.

Jaw member 272 includes a more-rigid structural body 274 and a more-compliant jaw liner 290. Structural body 274 enables pivotable coupling of jaw member 272 with the inner support sleeve 220, operable coupling of jaw member 272 with outer drive sleeve 210, and supports jaw liner 290 thereon. Jaw liner 290 may be fabricated from a compliant material such as, for example, polytetrafluoroethylene (PTFE), such that blade 234 is permitted to vibrate while in contact with jaw liner 290 without damaging components of ultrasonic surgical instrument 10, e.g., structural body 274 of jaw member 272, and without compromising the hold on tissue clamped between jaw member 272 and blade 234.

Figure 2:
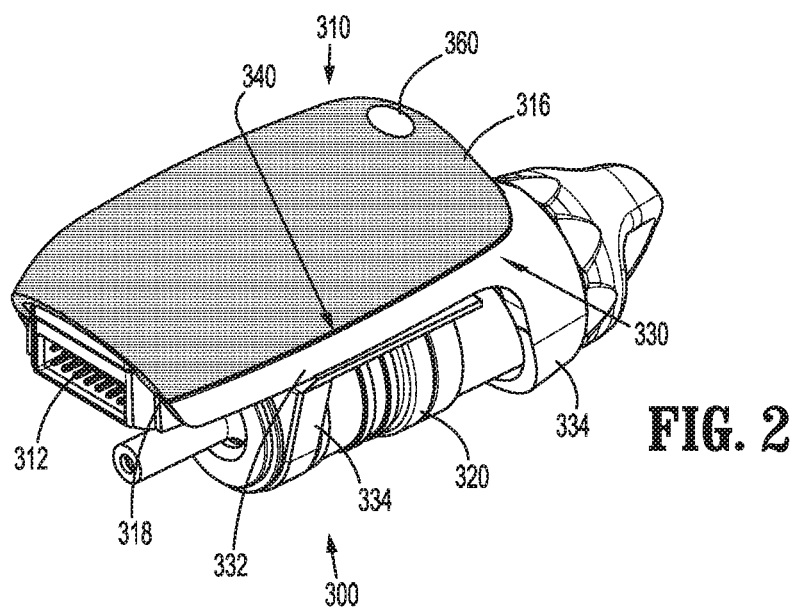
FIG. 2 is a front, perspective view of a transducer and generator assembly of the ultrasonic surgical instrument of FIG. 1.
Figure 3:
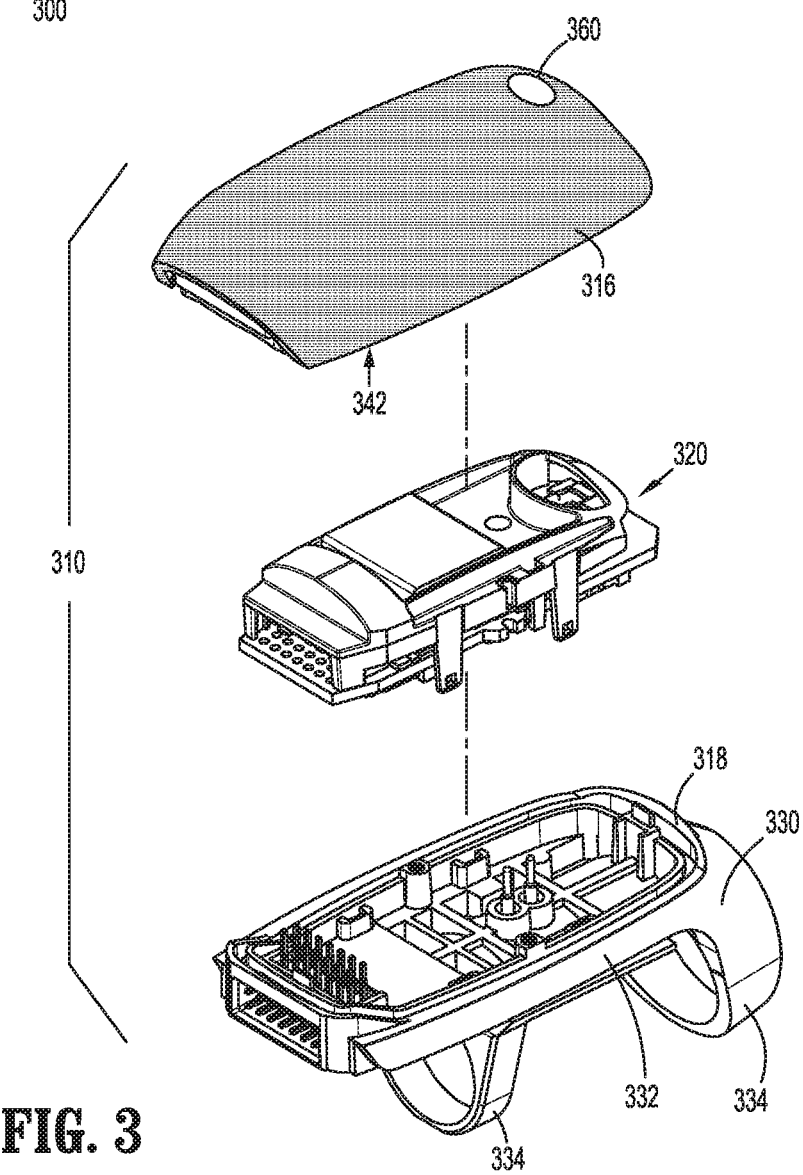
FIG. 3 is an exploded, perspective view of the transducer and generator assembly of FIG. 2.
Figure 4:
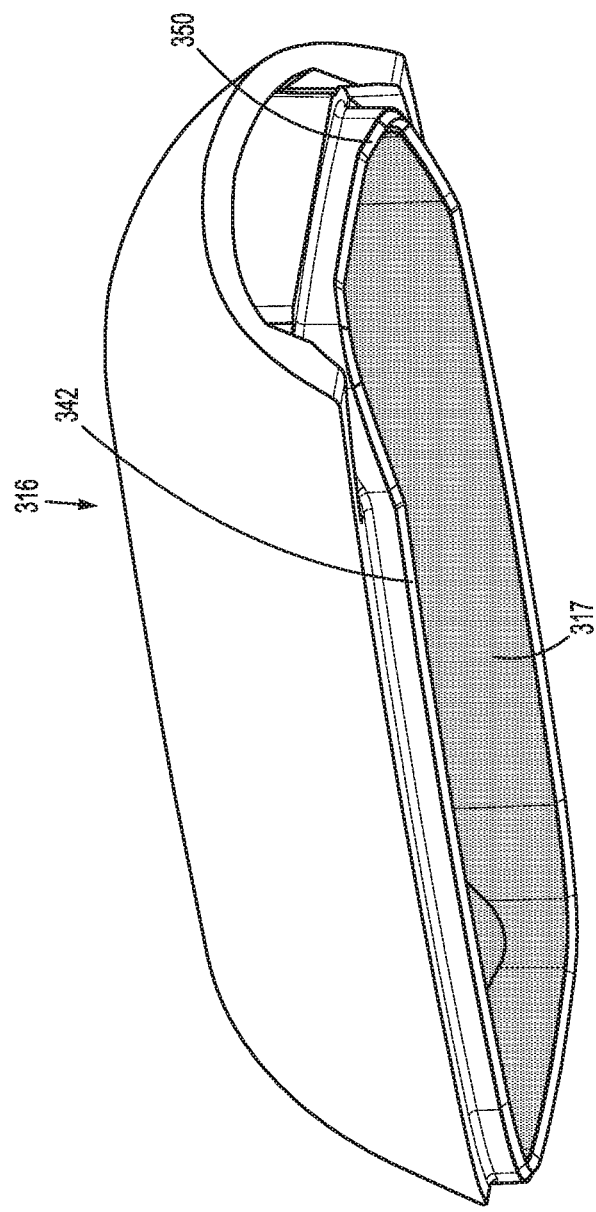
FIG. 4 is an enlarged, bottom, perspective view of an upper casing component of the generator of the transducer and generator assembly of FIG. 2.
Figure 5:
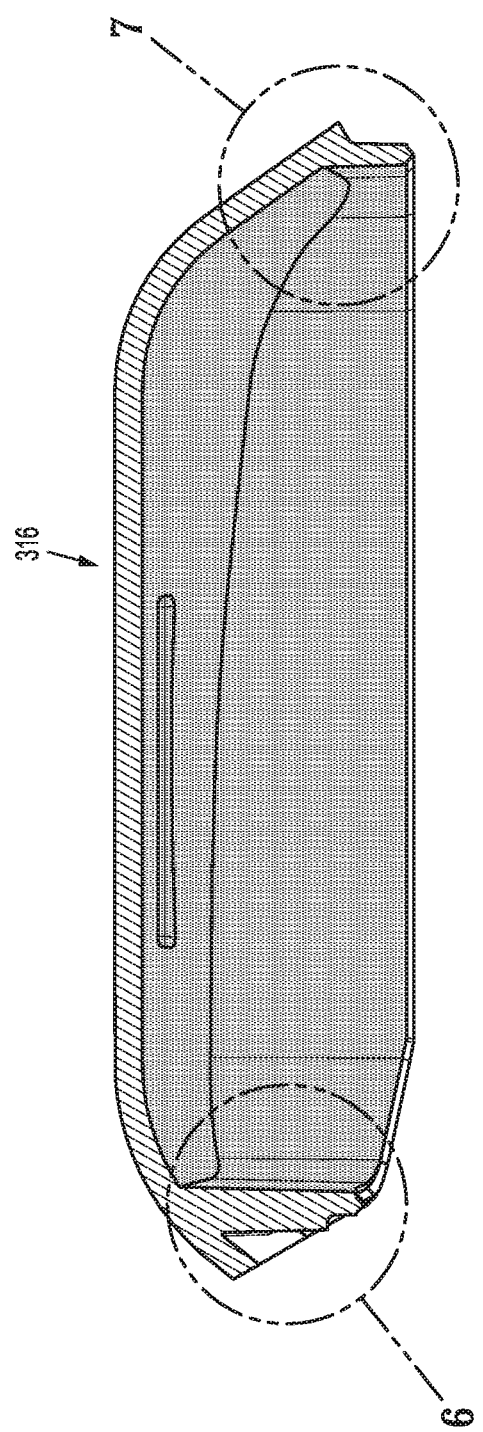
FIG. 5 is a side, longitudinal, cross-sectional view of the upper casing component of FIG. 4.
Figure 6:
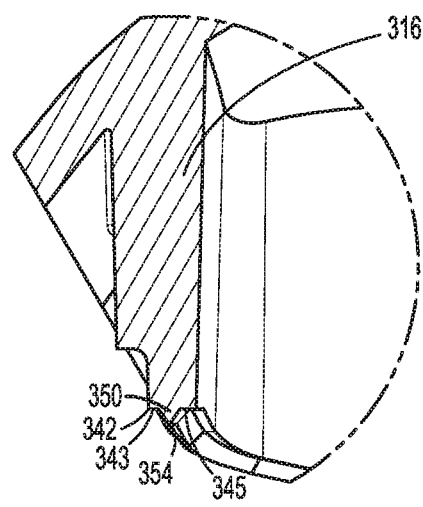
FIG. 6 is an enlarged, side, longitudinal, cross-sectional view of the area of detail indicated as "6" in FIG. 5.
Figure 7:
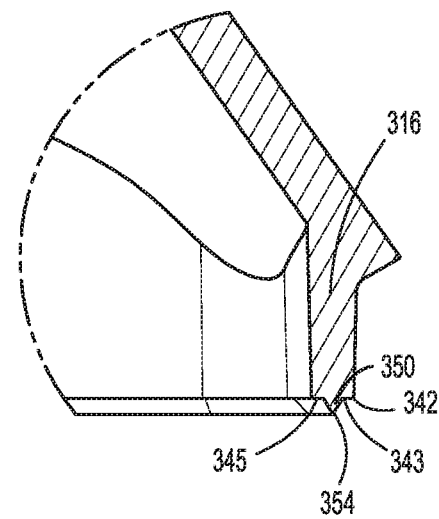
FIG. 7 is an enlarged, side, longitudinal, cross-sectional view of the area of detail indicated as "7" in FIG. 5.

Referring to FIGS. 1-3, TAG 300 is configured to slide into engagement partially within a recess 118 of body portion 112 of housing 110 of handle assembly 100 and includes, as noted above, generator assembly 310 and ultrasonic transducer assembly 320. TAG 300 further includes a support body 330 including a base 332 that supports generator assembly 310 thereon and a plurality, e.g., two, cradles 334 that rotatably support ultrasonic transducer assembly 320 thereon. Generator assembly 310 is electrically coupled with ultrasonic transducer assembly 320 via a slide contact assembly (not shown) to enable the transmission of drive signals from generator assembly 310 to ultrasonic transducer assembly 320 regardless of the rotational orientation of ultrasonic transducer assembly 320 relative to generator assembly 310. Generator assembly 310 includes an electrical connector 312 configured to engage a corresponding electrical connector (not shown) defined within body portion 112 of housing 110 of handle assembly 100 to electrically couple generator assembly 310 with handle assembly 110 when engaged thereon. More specifically, generator assembly 310 is electrically coupled with the battery assembly and activation button 120 via the electrical coupling of electrical connector 312 with the corresponding electrical connector of handle assembly 110.

Generator assembly 310 includes an enclosure 314 that sealingly encloses the electronics 320 of generator assembly 310 to hermetically seal the electronics 320 within enclosure 314. Enclosure 314 includes an upper casing component 316 and a lower casing component 318, although it is also contemplated that enclosure 314 be formed from more than two casing components and/or of different casing components, e.g., front and back casing components. Each of upper casing component 316 and lower casing component 318 may be formed from a high temperature resistant plastic, e.g., polyphenylsulfone (PPSU), polyaryletherketone, polyether ether ketone, polyetherimide, a liquid-crystal polymer, etc. Lower casing component 318 may be formed integrally with, e.g., via molding, base 332 of support body 330, or may be formed separately therefrom and attached thereto in any suitable manner, e.g., via adhesives, ultrasonic welding, mechanical attachment, etc.

With reference to FIGS. 4-7, in conjunction with FIGS. 2 and 3, enclosure 314 is formed to hermetically seal the electronics 320 of generator assembly 310 therein via ultrasonically welding upper casing component 316 to lower casing component 318. More specifically, enclosure 314 is hermetically sealed, via ultrasonic welding, along a weld seam 340 defined between opposing weld decks, e.g., a weld deck 342 of upper casing component 316 and a corresponding weld deck (not shown) of lower casing component 318 (FIGS. 2-3), formed on the outer perimeters of upper casing component 316 and lower casing component 318 (FIGS. 2-3). Weld seam 340 defines a non-planar configuration in that a single plane cannot be defined between the opposing weld deck 342 of upper casing component 316 and the corresponding weld deck of lower casing component 318 (FIGS. 2-3) along the entire weld seam 340. More specifically, a first portion of the weld seam 340 may define a first plane while a second portion of the weld seam 340 defines a second, different plane, e.g., that is disposed at an angle relative to the first plane, parallel and spaced-apart from the first plate, etc. Additional, e.g., third, fourth, etc., portions of weld seam 340 may likewise define different planes. Alternatively or additionally, weld seam 340 may define a non-planar portion(s) such as, for example, one or more curved portions. Put another way, weld seam 340 is defined in three dimensions.

The non-planar or three-dimensional configuration of weld seam 340 is a result of the non-planar or three-dimensional configurations of weld deck 342 of upper casing component 316 and the corresponding weld deck of lower casing component 318 (FIGS. 2-3) which, in turn, are non-planar to accommodate one or more features of generator assembly 310 such as, for example, electrical connector 312 (FIGS. 2-3). However, ultrasonically welding a non-planar or three-dimensional weld seam 340 is challenging in that, with a non-planar or three-dimensional weld seam 340, the distance from the head of the ultrasonic welder (not shown, used to create the ultrasonic weld along weld seam 340) to the weld seam 340 varies along the weld seam 340. More specifically, the head of the ultrasonic welder may be closer to the weld seam 340 at a first location and further from the weld seam 340 at a second, different location. As a result, the heating required, time required, etc. for forming a hermetically sealed ultrasonic weld at the first location of the weld seam 340 may be different from that at the second location of the weld seam 340.

In order to overcome the above-noted differences and ensure a suitable hermetically sealed ultrasonic weld along the entire weld seam 340, one of the components, e.g., upper casing component 316, is provided with an energy director 350 on the weld deck 342 thereof that is configured to facilitate formation of a hermetically-sealed weld seam 340 about the entire weld seam 340. Energy director 350, more specifically, extends from the planar surface defined by weld deck 342 and defines a width less than a width at the planar surface of weld deck 342 such that a planar surface portion 343, 345 of weld deck 342 is disposed on either side of energy director 350. Energy director 350 defines a base 352 at weld deck 342 having the maximum width of energy director 350. Energy director 350 extends away from base 352, tapering in width, to an apex 354.

In embodiments, energy director 350 defines a height of from about 0.025 to about 0.035 inches; in other embodiments, from about 0.027 to about 0.032 inches; and, in still other embodiments, about 0.030 inches. The term "about" is utilized herein to include generally accepted tolerances, e.g., manufacturing tolerances, material tolerances, environmental tolerances, measurement tolerances, etc.

In embodiments, energy director 350 defines a maximum width, at base 352, of from about 0.025 to about 0.035 inches; in other embodiments, from about 0.027 to about 0.032 inches; and, in still other embodiments, about 0.030 inches.

In embodiments, energy director 350 defines a maximum width to height ratio of about 0.75:1.0 to about 1.0:0.75; in other embodiments, from about 0.9:1.0 to about 1.0:0.9; and, in still other embodiments, of about 1.0:1.0.

In embodiments, energy director 350 defines an apex angle of from about 45 to about 75 degrees; in other embodiments, from about 55 to about 65 degrees; and in still other embodiments, about 60 degrees.

In embodiments, the width of weld deck 342 at the planar surface thereof is varied such as, for example, where a first width is defined along one end and/or side or portions thereof and a second width is defined along another end and/or side or a different portion of the end and/or side. In embodiments, weld deck 342 defines a first width, at the planar surface thereof, of from about 0.050 to about 0.060 inches; in other embodiments, from about 0.053 to about 0.058 inches; and, in still other embodiments, about 0.056 inches. In embodiments, weld deck 342 defines a second width at the planar surface thereof along a second portion thereof of from about 0.058 to about 0.068 inches; in other embodiments, from about 0.060 to about 0.065 inches; and, in still other embodiments, about 0.063 inches.

Further, in embodiments, each planar surface portion 343, 345 of weld deck 342 defines a width of from about 0.010 to about 0.020 inches. Each planar surface portion 343, 345 of weld deck 342 may, more specifically, in embodiments, define a width of from about 0.011 inches to about 0.015 inches, e.g., where the planar surface of the weld deck 342 defines the first width along the first portion, and/or, in embodiments, defines a width of from about 0.015 inches to about 0.019 inches, e.g., where the planar surface of the weld deck 342 defines the second width along the second portion.

In embodiments, a ratio of the maximum width of energy director 350 to the width of weld deck 342 (or a portion thereof, e.g., a first portion) at the planar surface is about 0.45:1.0 to about 0.65:1.0; in other embodiments about 0.50:1.0 to about 0.60:1.0; and in still other embodiments, from about 0.53:1.0 to about 0.54:1.0. Additionally or alternatively, a ratio of the maximum width of energy director 350 to the width of weld deck 342 (or a portion thereof, e.g., a second portion) at the planar surface is about 0.42:1.0 to about 0.52:1.0; in other embodiments about 0.45:1.0 to about 0.49:1.0; and in still other embodiments, from about 0.47:1.0 to about 0.48:1.0. Overall (e.g., in the first and second portions), the ratio may be from about 0.40:1.0 to about 0.65:1.0.

Figure 8:
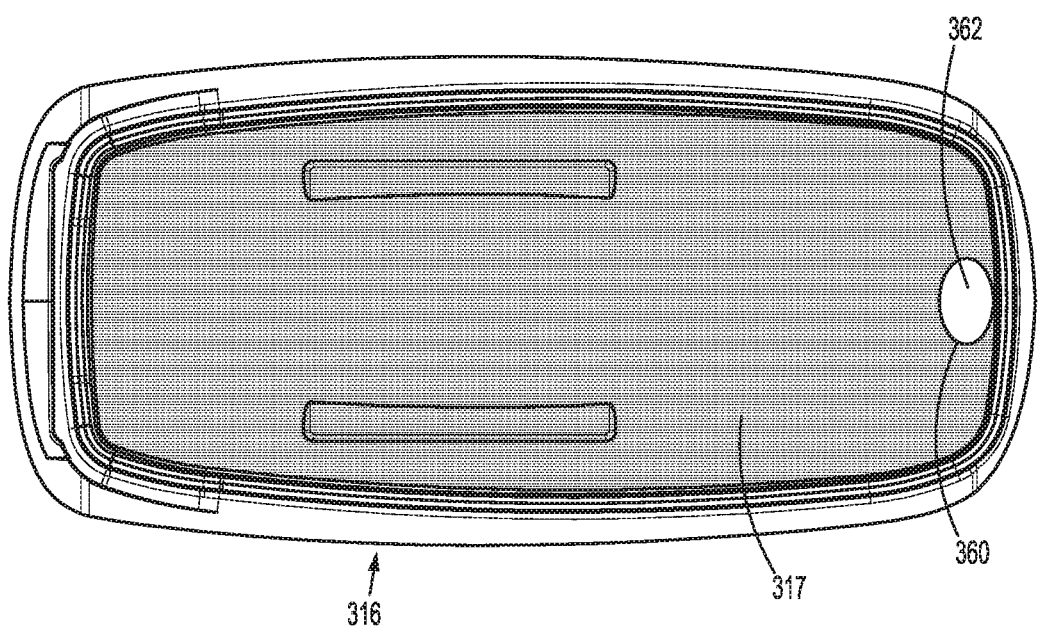
FIG. 8 is a bottom view of the upper casing component of FIG. 4.

With reference to FIG. 8, in embodiments, upper casing component 316 (and, in embodiments both upper casing component 316 and lower casing component 318 (FIGS. 2-3)) is formed from a substantially transparent or material, e.g., transparent PPSU, where "substantially transparent" includes transparencies of 90% or greater. The interior surface of upper casing component 316 (although it may alternatively or additionally be the exterior surface) is then laser etched or otherwise treated to define a finish 317 that has a decreased transparency, e.g., decreased by 50%, 75%, 90%, etc., compared to non-treated PPSU, or is rendered substantially opaque (wherein "substantially opaque" includes opacities of 90% or greater). The entire interior surface (or a substantial portion) of upper casing component 316 is treated in this manner to achieve finish 317, except for one or more indicator windows 360, which remain transparent without any finish. In embodiments, the one or more indicator windows 360 are also treated to define a finish 362 but to a lesser extent than the remainder of the interior surface of upper casing component 316 such that the finish 362 of the one or more indicator windows 360 is more transparent than the finish 317. For example, the finish 317 may be achieved by laser etching using a first power while the finish 362 is achieved by laser etching using a second, lower power. The first power may be, in embodiments, at least 10 Watts; in other embodiments, at least 14 Watts; in still other embodiments, at least 18 Watts. The second power may be, in embodiments, at most 6 Watts; in other embodiments, at most 4 Watts; and, in still other embodiments, at most 2 Watts.

In embodiments, the one or more indicator windows 360, including no finish or finish 362, are defined on upper casing component 316 to coincide with, e.g., in registration above or otherwise positioned relative to, LED's or other visual indicators, e.g., OLED's, incandescent light source, etc., of the electronics 320 of generator assembly 310 (see FIGS. 2-3) such that a user can visually verify the illumination of one or more of the LEDs, the color of the illuminated LED(s), an illumination pattern, etc. through the one or more indicator windows 360 of upper casing component 316. The remainder of the interior of generator assembly 310 is obscured; that is, visibility through upper casing component 316 into the interior of generator assembly 310 is substantially occluded due to the less transparent or opaque finish 317.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An enclosure configured to hermetically seal electronics of a surgical instrument therein, the enclosure comprising:
   a first casing component defining a first weld deck about a perimeter thereof;
   a second casing component defining a second weld deck about a perimeter thereof; and
   an energy director extending from the first weld deck and configured to facilitate ultrasonic welding of the first and second weld decks of the first and second casing components, respectively, with one another to establish a weld seam hermetically sealing the first and second casing components,
   wherein the first weld deck lies in multiple planes.

2. The enclosure according to claim 1, wherein the energy director defines a maximum width less than a width of the first weld deck.

3. The enclosure according to claim 2, wherein the first weld deck includes first and second planar portions disposed on first and second sides of the energy director.

4. The enclosure according to claim 1, wherein the first weld deck includes a first portion defining a first width and a second portion defining a second, different width.

5. The enclosure according to claim 1, wherein a ratio of a maximum width of the energy director to a width of at least a portion of the first weld deck is about 0.40:1.0 to about 0.65:1.0.

6. The enclosure according to claim 1, wherein the first and second casing components are formed from polyphenylsulfone (PPSU).

7. An enclosure configured to hermetically seal electronics of a surgical instrument therein, the enclosure comprising:
   a first casing component; and
   a second casing component,
   wherein the first and second casing components are ultrasonically welded to one another along a weld seam extending about perimeters of the first and second casing components, the weld seam defining a non-planar configuration.

8. The enclosure according to claim 7, wherein the first and second casing components include first and second weld decks, respectively, ultrasonically welded to one another to define the weld seam, and wherein each of the first and second weld decks defines a non-planar configuration.

9. The enclosure according to claim 8, wherein the first weld deck includes an energy director extending therefrom, the energy director configured to facilitate ultrasonic welding of the first and second weld decks to one another.

10. The enclosure according to claim 8, wherein a width of at least one of the first or second weld decks varies about the perimeter of the respective first or second casing component.

11. The enclosure according to claim 7, wherein the ultrasonically welded first and second casing components define a hermetically sealed interior volume.

12. The enclosure according to claim 11, further comprising surgical instrument electronics disposed within the hermetically sealed interior volume.

13. The enclosure according to claim 12, wherein the surgical instrument electronics include at least one of a generator or a battery.

14. The enclosure according to claim 7, wherein at least one of the first or second casing components is formed from polyphenylsulfone (PPSU).

15. An enclosure configured to hermetically seal electronics of a surgical instrument therein, the enclosure comprising:
- a first casing component defining a first weld deck;
- a second casing component defining a second weld deck; and
- an energy director extending from the first weld deck and configured to facilitate ultrasonic welding of the first and second weld decks to one another to form a weld seam that defines a non-planar configuration.

16. The enclosure according to claim 15, wherein the weld seam includes a first portion and a second portion, and wherein the first and second portions are disposed at an angle relative to one another.

17. The enclosure according to claim 16, wherein each of the first and second portions is planar.

18. The enclosure according to claim 16, wherein the weld seam further includes a third portion disposed at an angle relative to the first and second portions.

19. The enclosure according to claim 16, where the first portion defines a first width and the second portion defines a second, different width.

20. The enclosure according to claim 15, wherein the first and second casing components are formed from polyphenylsulfone (PPSU).

* * * * *